US012194196B2

(12) United States Patent
Ratner et al.

(10) Patent No.: US 12,194,196 B2
(45) Date of Patent: Jan. 14, 2025

(54) PRO-HEALING ELASTIC ANGIOGENIC MICROPOROUS VASCULAR GRAFT

(71) Applicant: University of Washington, Seattle, WA (US)

(72) Inventors: Buddy D. Ratner, Seattle, WA (US); Le Zhen, Seattle, WA (US); Felix Simonovsky, Seattle, WA (US); Jonathan Himmelfarb, Seattle, WA (US)

(73) Assignee: University of Washington, Seattle, WA (US)

( * ) Notice: Subject to any disclaimer, the term of this patent is extended or adjusted under 35 U.S.C. 154(b) by 163 days.

(21) Appl. No.: 16/861,104

(22) Filed: Apr. 28, 2020

(65) Prior Publication Data

US 2020/0261207 A1    Aug. 20, 2020

Related U.S. Application Data

(63) Continuation of application No. 15/879,301, filed on Jan. 24, 2018, now Pat. No. 10,667,897.

(60) Provisional application No. 62/449,984, filed on Jan. 24, 2017.

(51) Int. Cl.
| *A61F 2/06*   | (2013.01) |
| *A61L 27/18*  | (2006.01) |
| *A61L 27/34*  | (2006.01) |
| *A61L 27/50*  | (2006.01) |
| *A61L 27/56*  | (2006.01) |
| *A61L 33/00*  | (2006.01) |

(52) U.S. Cl.
CPC .............. *A61L 27/507* (2013.01); *A61F 2/06* (2013.01); *A61L 27/18* (2013.01); *A61L 27/34* (2013.01); *A61L 27/56* (2013.01); *A61L 33/0011* (2013.01); *A61F 2250/0023* (2013.01); *A61F 2250/0039* (2013.01); *A61F 2250/0067* (2013.01); *A61L 2300/412* (2013.01); *A61L 2300/42* (2013.01)

(58) Field of Classification Search
CPC ........ A61L 27/507; A61L 27/18; A61L 27/34; A61L 27/56
See application file for complete search history.

(56) References Cited

U.S. PATENT DOCUMENTS

| 7,022,135 B2 | 4/2006 | Zilla et al. |
| 7,972,628 B2 | 7/2011 | Ratner et al. |
| 2006/0009839 A1 | 1/2006 | Tan |
| 2007/0042017 A1 | 2/2007 | Kutryk et al. |
| 2008/0075752 A1* | 3/2008 | Ratner .................... A61P 41/00 424/426 |
| 2015/0238306 A1 | 8/2015 | Marshall et al. |
| 2015/0320542 A1* | 11/2015 | Gabriele .................. A61F 2/88 623/1.13 |

(Continued)

OTHER PUBLICATIONS

Bascom, J.U., "Gelatin Sealing to Prevent Blood Loss From Knitted Arterial Grafts," Surgery 50(3):504-512, Sep. 1961.

(Continued)

*Primary Examiner* — Suba Ganesan
(74) *Attorney, Agent, or Firm* — Christensen O'Connor Johnson Kindness

(57) ABSTRACT

Synthetic polymeric vascular grafts that promote endothelial healing and methods of their preparation and use are provided.

17 Claims, 13 Drawing Sheets

(56) References Cited

U.S. PATENT DOCUMENTS

2016/0302911 A1 10/2016 Soletti
2018/0206971 A1 7/2018 Ratner et al.

OTHER PUBLICATIONS

Benrashid, E., et al., "Tissue Engineered Vascular Grafts: Origins, Development, and Current Strategies for Clinical Application," Methods 99:13-19, Apr. 2016.
Doi, K., and T. Matsuda, "Enhanced Vascularization in a Microporous Polyurethane Graft Impregnated With Basic Fibroblast Growth Factor and Heparin," Journal of Biomedical Materials Research 34(3):361-370, Mar. 1997.
Dukkipati, R., "Biological Grafts for Hemodialysis Access: Historical Lessons, State-of-the-Art and Future Directions," Seminars in Dialysis 26(2):233-239, Mar.-Apr. 2013.
G, N., et al., "Tissue Engineering Vascular Grafts a Fortiori: Looking Back and Going Forward," Expert Opinion on Biological Therapy 15(2):231-244, Feb. 2015.
Hisu, S.-H., et al., "Comparative In Vitro Evaluation of Two Different Preparations of Small Diameter Polyurethane Vascular Grafts," Artificial Organs 24(2):119-128, Feb. 2000.
Hsu, S.-H., et al., "Improved Retention of Endothelial Cells Seeded on Polyurethane Small-Diameter Vascular Grafts Modified by a Recombinant RGD containing Protein," Artificial Organs 27(12):1068-1078, Dec. 2003.
Matsuda, M., and Y. Nakayama, Surface Microarchitectural Design in Biomedical Applications: In Vitro Transmural Endothelialization on Microporous Segmented Polyurethane Films Fabricated Using an Excimer Laser, Journal of Biomedical Material Research 31(2):235-242, Jun. 1996.

Ota, K., "Towards an Ideal Polyurethane Graft for Hemodialysis," Journal of Biomaterials Applications 4(2):141-157, Oct. 1989.
Pennel, T., et al., "The Performance of Cross-Linked Acellular Arterial Scaffolds as Vascular Grafts; Pre-Clinical Testing in Direct and Isolation Loop Circulatory Models," Biomaterials 35(24):6311-6322, Aug. 2014.
Wang, Z., et al., "Functionalization of Electrospun Poly($\varepsilon$-Caprolactone) Scaffold With Heparin and Vascular Endothelial Growth Factors for Potential Application As Vascular Grafts," Journal of Bioactive and Compatible Polymers 28(2):154-166, 2013.
Zdrahala, R.J., "Small Caliber Vascular Grafts. Part II: Polyurethanes Revisited," Journal of Biomaterials Applications 11(1):37-61, Jul. 1996.
Zhen, L., et al., "6IXS Vascular Solutions: Dramatically Improves the Success Rates of Synthetic Grafts for Vascular Surgeries by Optimizing Healing," Poster Presentation, Science and Technology Showcase, University of Washington, Jan. 21, 2016, Seattle, Wash., 1 page.
Bergel, D.H., "The Static Elastic Properties of the Arterial Wall," Journal of Physiology 156(3):445-457, May 1961.
"BMES 2016," Biomedical Engineering Society™: Advancing Human Health and Well Being™, 2016 Annual Meeting, Oct. 5-8, 2016, Minneapolis, Minn., See p. 214 of 256-page program, "Precision-Engineered Porous Material With Turnable Mechanical Property for Vascular Graft Application," Le Zhen and Buddy Ratner.
Clowes, A.W., et al., "Mechanisms of Arterial Graft Healing. Rapid Transmural Capillary Ingrowth Provides a Source of Intimal Endothelium and Smooth Muscle in Porous PTFE Prostheses," American Journal of Pathology 123(2):220-230, May 1986.
Kohler, T.R., and T.R. Kirkman, "Dialysis Access Failure: A Sheep Model of Rapid Stenosis," Journal of Vascular Surgery 30(4):744-751, Oct. 1999.

\* cited by examiner

PRO-HEALING ELASTIC ANGIOGENIC MICROPOROUS VASCULAR GRAFT

CROSS-REFERENCE TO RELATED APPLICATIONS

This application is a continuation of application Ser. No. 15/879,301, filed Jan. 24, 2018, which claims the benefit of U.S. Provisional Application No. 62/449,984 filed Jan. 24, 2017, each expressly incorporated herein by reference in its entirety.

BACKGROUND OF THE INVENTION

In the United States, 17% of overall national health expenditures are linked to cardiovascular diseases. $50 billion are spent annually on end stage renal disease (ESRD). Cardiovascular disease and the treatment of ESRD often require synthetic vascular grafts. Almost 1.4 million vascular grafts are needed every year in the US alone. However, the success rate of current synthetic vascular grafts in many vascular sites is low. For example, arteriovenous Teflon grafts, the most prevalent graft in the market for hemodialysis, has a failure rate of 50% in one year.

The most common causes of vascular graft failure are thrombosis and intimal hyperplasia (excessive cell growth). The mismatch of mechanical properties of the currently used rigid vascular graft materials (e.g., ePTFE and Dacron) and elastic native blood vessels contributes to turbulence and repeated damage to the native blood vessel under the cyclical, pulsatile blood flow, and suboptimal blood compatibility of current vascular graft materials induces thrombosis. Additionally, in healthy native blood vessels, a single layer of endothelial cells forms an inner lining called the endothelium that can suppress smooth muscle cell proliferation or intimal hyperplasia, which is another major cause of vascular graft failures. Another serious complication of vascular grafts is infection. Current biomaterials generally elicit a cascade of reactions (foreign body reaction, or FBR) orchestrated by macrophages that result in a scar layer that separate the material from the rest of the body, creating heavens for bacterial infections.

These complications can be addressed by development of synthetic vascular grafts that have mechanical properties tunable to match those of the native blood vessels; sufficient strength to withstand suture; be stable in the body in the long term, and promote complete healing of a healthy endothelial cell layer on the luminal surface of the synthetic vascular grafts. Even though synthetic graft materials having some of these characteristics have been developed, complete healing of endothelium in synthetic vascular grafts has not been demonstrated to date. Thus, a need exists for a synthetic vascular prosthesis that has physical properties matching those of a native blood vessel and at the same time promotes endothelial healing.

SUMMARY OF THE INVENTION

In one aspect, provided herein is a vascular graft comprising a compliant, elastomeric polymeric graft wall having a luminal surface adapted for contact with blood flow, wherein the graft wall has interconnected pores throughout the graft wall connecting the outer surface of the graft wall to the luminal surface of the graft wall, wherein each pore of the interconnected pores has a substantially uniform pore size, and wherein the pore size is in the range from about 25 μm to about 85 μm, and wherein the luminal surface is coated with a layer of endothelial cell growth substrate. In some embodiments, the pore size is in the range from about 30 μm to about 50 μm or about 40 μm. In other embodiments, the graft wall allows blood vessel growth through the wall to the luminal surface.

In some embodiments, the polymeric graft wall comprises a crosslinked polyurethane comprising one or more soft segments and one or more hard segments, wherein the molar ratio of soft segments to hard segments is between about 0.1 to about 0.6, between about 0.1 and about 0.4, between about 0.125 and about 0.22, about 0.125, about 0.36, or about 0.22.

In certain embodiments, the layer of endothelial cell growth substrate has thickness of between about 5 μm and about 500 μm. In other embodiments, the endothelial cell growth substrate is biodegradable and/or comprises gelatin, agarose gel, hydroxypropyl methylcellulose, or albumin gel.

In some embodiments, the graft wall further comprises a reinforcement material embedded within the graft wall, for example, a non-degradable knitted or woven polymeric mesh.

In certain embodiments, the graft wall has one or more characteristics selected from: suture strength from about 0.5 N to about 5.0 N; burst pressure over 1600 mm Hg; and a Young's Modulus between about 200 kPa and 850 kPa.

In particular embodiments, the graft has a wall thickness substantially the same as the wall thickness of a native blood vessel, such as an artery or vein.

In some embodiments, the graft wall is biostable. In certain embodiments, the endothelial cell growth substrate is biodegradable and optionally comprises an anti-thrombogenic agent, such as heparin, disintegrin, hirudin, or a combination thereof.

In certain embodiments, the graft is elastic, suturable, kink-resistant, sterilizable, biocompatible, biostable, shelf-stable; has compliance matching with natural blood vessel, has a wall thickness substantially similar to that of a native blood vessel; has low thrombogenicity and does not elicit inflammatory response.

In some embodiments, the graft comprises the following elements: a polymeric graft wall having a network of interconnected pores spanning the graft wall from the outer surface to the luminal surface, wherein all pores are uniform in size and about 40 microns; a compliance (elasticity) similar to the native blood vessel; and a biodegradable luminal surface coating that can assist in the regeneration of an endothelial cell lining.

In a second aspect, provided herein is a method of making a vascular graft comprising:
  (a) coating a cylindrical rod having an outer surface and a first radius with a layer of an endothelial cell growth substrate to provide a coated rod;
  (b) positioning the coated rod in the center of a tube having a second radius greater than the first radius wherein the second radius is the inner radius of the tube;
  (c) filling the space between the outer surface of the coated rod and the inner wall of the tube with a polymer scaffold template comprising an array of monodisperse porogens, wherein substantially all the porogens have a similar diameter, wherein the mean diameter of the porogens is between about 25 and about 85 micrometers, wherein substantially all porogens are each connected to at least 4 other porogens, and wherein the diameter of substantially all the connections between the porogens is between about 15% and about 40% of the mean diameter of the porogens;

(d) forming a polymer around the polymer scaffold template;

(e) removing the polymer scaffold template to produce a porous polymeric graft wall, and (f) removing the rod and the tube, thereby producing the vascular graft.

In a third aspect, provided herein is method for treating vascular disease, comprising the step of implanting into a mammal in need of treatment a vascular graft, wherein the vascular graft comprises a polymeric graft wall having a luminal surface, wherein the graft wall has a plurality of interconnected pores connecting the outer surface of the graft with the luminal surface, wherein each pore of the interconnected pores has a substantially uniform pore size, and wherein the mean diameter of the pores is between about 25 µm to about 85 µm, and wherein the luminal surface is coated with a layer of endothelial cell growth substrate.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

In one aspect, the invention provides a vascular graft. As used herein, "vascular graft" or "graft" refers to a flexible tubular structure or a patch that can be coupled directly to native blood vessels. The vascular graft of the invention comprises a compliant, elastomeric polymeric graft wall having a luminal surface adapted for contact with blood flow, wherein the graft wall has a plurality of interconnected pores throughout the graft wall reaching from the outer surface of the graft to the luminal surface, wherein each pore of the interconnected pores has a substantially uniform pore size, and wherein the mean diameter of the pores is between about 25 µm to about 85 µm, and the luminal surface is coated with a layer of endothelial cell growth substrate.

As used herein, "substantially uniform pore size" means that substantially all pores have a similar diameter within the specified range. Two pores have a "similar diameter" when the difference in the diameters of the two pores is less than about 20% of the larger diameter. As used herein, "diameter of the pore" is defined as the longest line segment that can be drawn that connects two points within the pore. For example, for a graft with interconnected pores having a mean pore diameter of about 40 µm, "substantially uniform pore size" means a pore having a mean diameter that is 40 µm+/−10 µm, 40 µm+/−8 µm, 40 µm+/−5 µm, or 40 µm+/−2 µm.

Figure 2A:
FIG. 2A is an image of a cross section of the porous polyurethane graft with the average pore diameter of 40 µm implanted into a mouse tissue demonstrating that the graft material promotes blood vessel (black) growth through the graft pores (white).
Figure 2B:
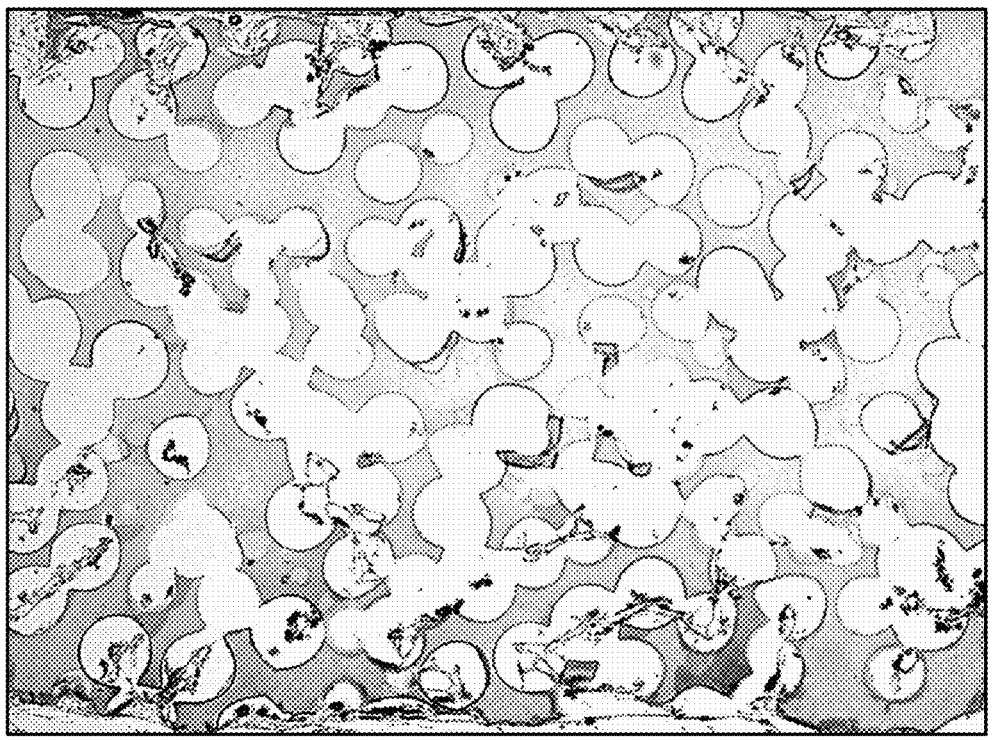
FIG. 2B is an image of cross section of the porous polyurethane graft with the average pore diameter of 100 µm implanted into a mouse tissue showing little to no blood vessel growth through the pores.

In some embodiments, the polymeric graft wall comprises a polymeric material having an array of pores, wherein substantially all the pores have a similar diameter, wherein the mean diameter of the pores is between about 25 µm to about 85 µm, wherein substantially all the pores are each connected to at least 4 other pores, and wherein the diameter of substantially all the connections between the pores is between about 15% and about 40% of the mean diameter of the pores. In some embodiments, the mean diameter of the pores is between about between about 25 µm to about 85 µm, between about 30 µm to about 60 µm, between about 30 µm to about 50 µm, or about 40 µm. As shown in FIGS. 2A and 2B, crosslinked polyurethane material with pores of the mean diameter of about 40 µm promotes higher blood vessel growth than material of the same chemical composition that has pores of the mean diameter of about 100 µm.

The pores in the graft wall described herein can have any suitable shape, such as roughly or perfectly spherical. In some embodiments, substantially all the pores are connected to between about 4 to about 12 other pores, such as between about 4 to about 7 other pores. In some embodiments, the vascular graft disclosed herein comprises a polymeric material described in U.S. Pat. No. 8,318,193, the disclosure of which is incorporated herein by reference.

In an exemplary embodiment, the polymeric graft wall comprises a crosslinked polyurethane material with precision engineered porous structure where spherical pores with a diameter of about 40 µm are interconnected by holes of about 13 µm in diameter, as shown in FIG. 2A. Each pore is interconnected to the neighboring pores by 10-12 holes, which make the whole material highly interconnected. Materials having such structure can elicit a healing and integration reaction from the body distinctively different from the classic foreign body reaction (FBR) by attracting macrophages to reside in the porous structure and turning them into a pro-healing state which orchestrates healing. (Sussman, Eric M., Michelle C. Halpin, Jeanot Muster, Randall T. Moon, and Buddy D. Ratner. 2014. Porous Implants Modulate Healing and Induce Shifts in Local Macrophage Polarization in the Foreign Body Reaction. Annals of Biomedical Engineering 42(7):1508-16.) As a result, a vascular graft comprising a graft disclosed herein having a wall with the precision-engineered microporous structure throughout the graft wall from the outer surface of the graft to the luminal surface can allow endothelial cells to grow through the vascular graft wall and cover the whole lumen of the vascular graft. This complete healing can also eliminate the defenseless regions in the biomaterial, which is likely to reduce vascular graft infection.

In some embodiments, the polymeric graft wall comprises a polyurethane. In certain embodiments, the polymer of the polymeric graft is a polyurethane. In certain embodiments, the polyurethane is crosslinked. In some embodiments, the crosslinked polyurethane polymer of the vascular graft wall comprises one or more soft segments and one or more hard segments. A "soft segment" is a material inclusion of which into a polymer imparts elasticity to the polymer. A "hard segment" is a material that imparts mechanical strength to the polymer.

Suitable soft segments can be derived from a hydroxyl terminated oligomer or polymer. Exemplary precursors of soft segments include poly(tetramethylene oxide) (PTMO), poly(ethylene oxide), poly(propylene oxide), hydroxyl terminated polydimethylsiloxane (PDMS), hydroxyl terminated poly(isoprene), hydroxyl terminated fluoropolymer, and combinations thereof. In some embodiments, the soft segment has average $M_n$ between about 200 Da to about 10,000 Da, 200 Da to about 5,000 Da, between about 300 Da to about 5,000 Da, or between about 300 Da and 1,000 Da.

Suitable precursors of the soft segments of the polyurethanes disclosed herein include poly(tetramethylene oxide) (PTMO), poly(ethylene oxide), poly(propylene oxide), hydroxyl terminated polydimethylsiloxane (PDMS), hydroxyl terminated poly(isoprene), hydroxyl terminated polyisobutylene, hydroxyl terminated fluoropolymer, hydroxyl terminated polysilane, and combinations thereof.

In some embodiments, the soft segment is a polyether. Exemplary polyethers suitable for the preparation of the polyurethanes used in the preparation of the vascular grafts include poly(tetramethylene oxide), poly(propylene oxide), and poly(ethylene oxide). In some embodiments, the soft segment derived from is poly(tetramethylene oxide). In other embodiments, the soft segment is derived from hydroxyl terminated polydimethylsiloxane (PDMS).

In some embodiments, hard segments are derived from diisocyanates. Exemplary diisocyanates useful for the preparation of the polymeric graft wall include 2,2'-methylene diphenyl diisocyanate, 2,4'-methylene diphenyl diisocyanate, 4,4'-methylene diphenyl diisocyanate, (MDI), toluene diisocyanate (TDI), naphthalene 1,5-diisocyanate (NDI), 1,6-hexamethylene diisocyanate (HDI), isophorone diisocyanate (IPDI), 4,4'-dicyclohexylmethane diisocyanate ($H_{12}$MDI), lysine diisocyanate, and combinations thereof.

In some embodiments, the polyurethane polymer is crosslinked by one or more residues of a crosslinker. Suitable crosslinkers include glycerol, 1,2,6-hexanetriol, hexane-1,3,5-triol, pentaerythritol (PT), and a combination thereof. In some embodiments, the crosslinker residue acts as a hard segment; typical crosslinkers acting as hard segments include 6-[3-(6-isocyanatohexyl)-2,4-dioxo-1,3-diazetidin-1-yl]hexyl N-(6-isocyanatohexyl)carbamate (HTI or Desmodur N-3200), 1,1,1-tris(hydroxymethyl) propane (TMP), tris(4-isocyanatophenyl) thiophosphate (TI), undecane-1,6,11-triyl triisocyanate (UTI), triphenylmethane-4,4',4"-triisocyanate (TPTI), and a combination thereof.

Figure 3:
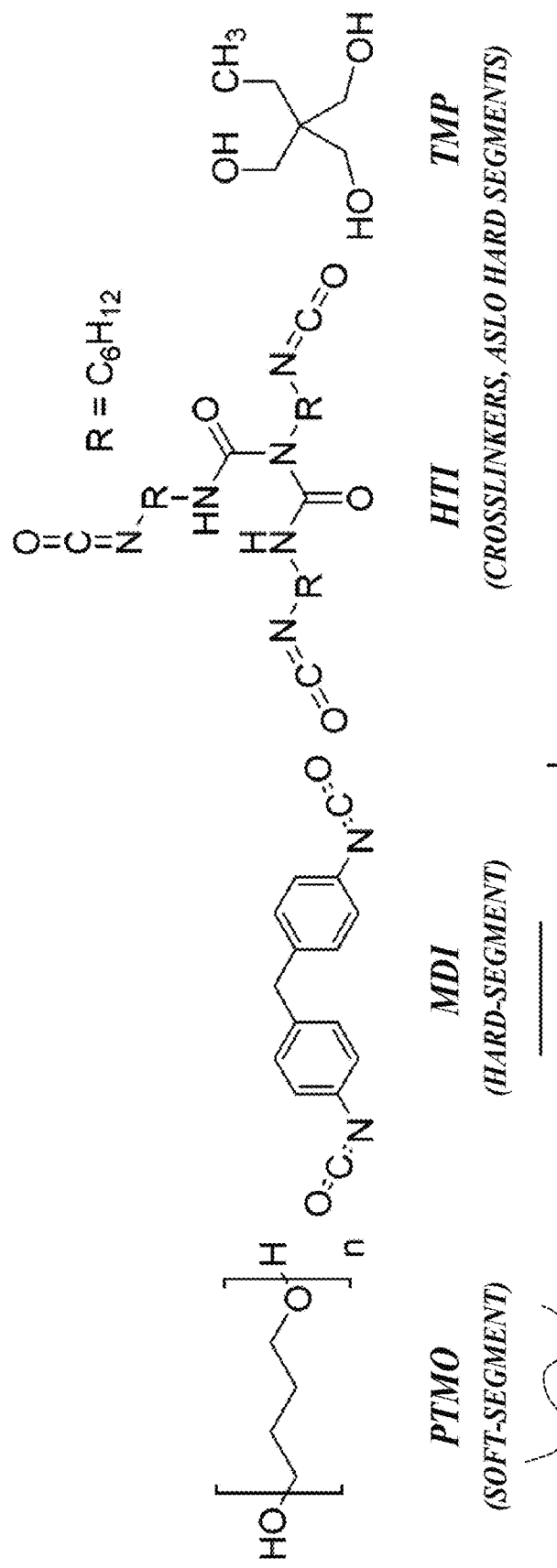
FIG. 3 is a schematic representation of the one-step, catalyst-free, solvent-free synthesis of a polyurethane used in the preparation of an exemplary graft resulting in a crosslinked polyurethane polymer having soft segments (dotted line) derived from PTMO and hard segments (solid lines) derived from diisocyanate (MDI) and crosslinkers (HTI and TMP).
Figure 3:
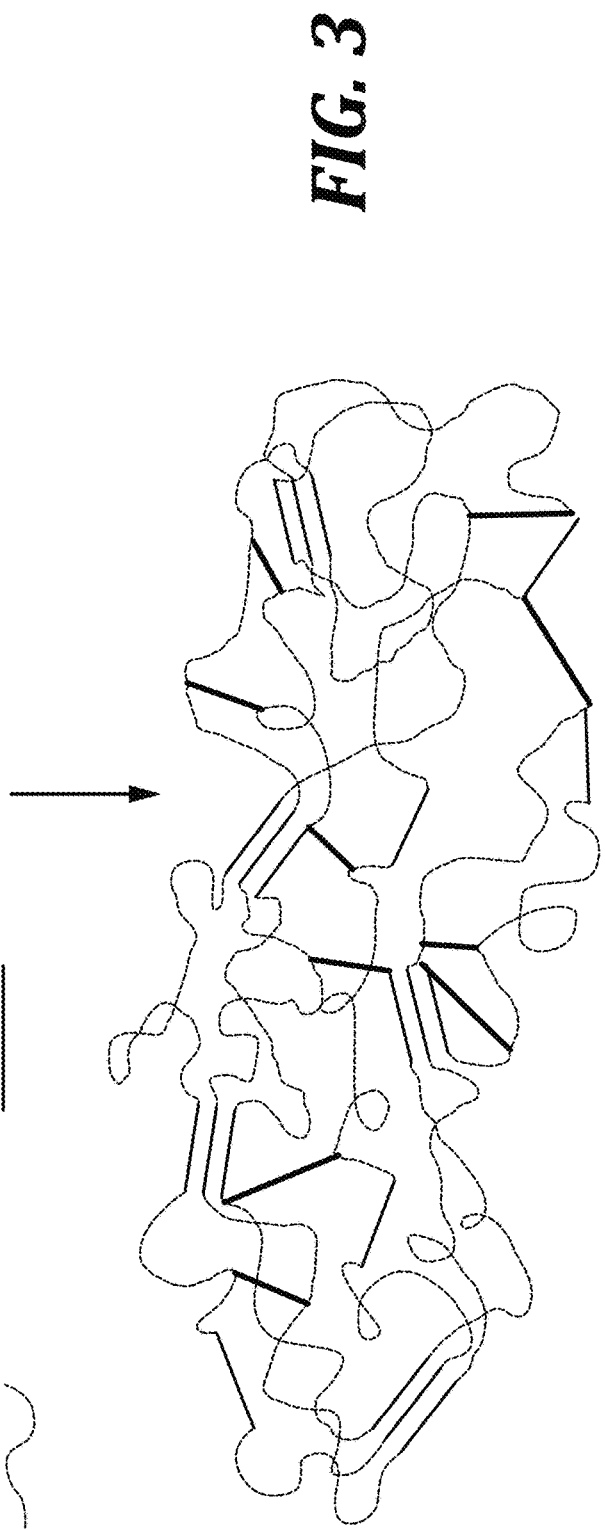

In one exemplary embodiment, the polymeric graft wall is prepared by co-polymerization of poly(tetramethylene oxide) (PTMO), 4,4'-methylene diphenyl diisocyanate, 6-[3-(6-isocyanatohexyl)-2,4-dioxo-1,3-diazetidin-1-yl]hexyl N-(6-isocyanatohexyl)carbamate, and 1,1,1-tris(hydroxymethyl) propane, as shown schematically in FIG. 3. In the four components used, PTMO is the soft segment, which gives the material elasticity. MDI is a part of the hard segment, which imparts mechanical strength into the material. HTI and TMP are crosslinkers, which hold the material together, preventing it from dissolving upon contact with organic solvents, for example, during extraction of porogenic template. Crosslinking HTI and TMP are also hard segments. In one exemplary embodiment, the molar ratio of PTMO/MDI/HTI/TMP is 4/3/4/4.

Figure 4:
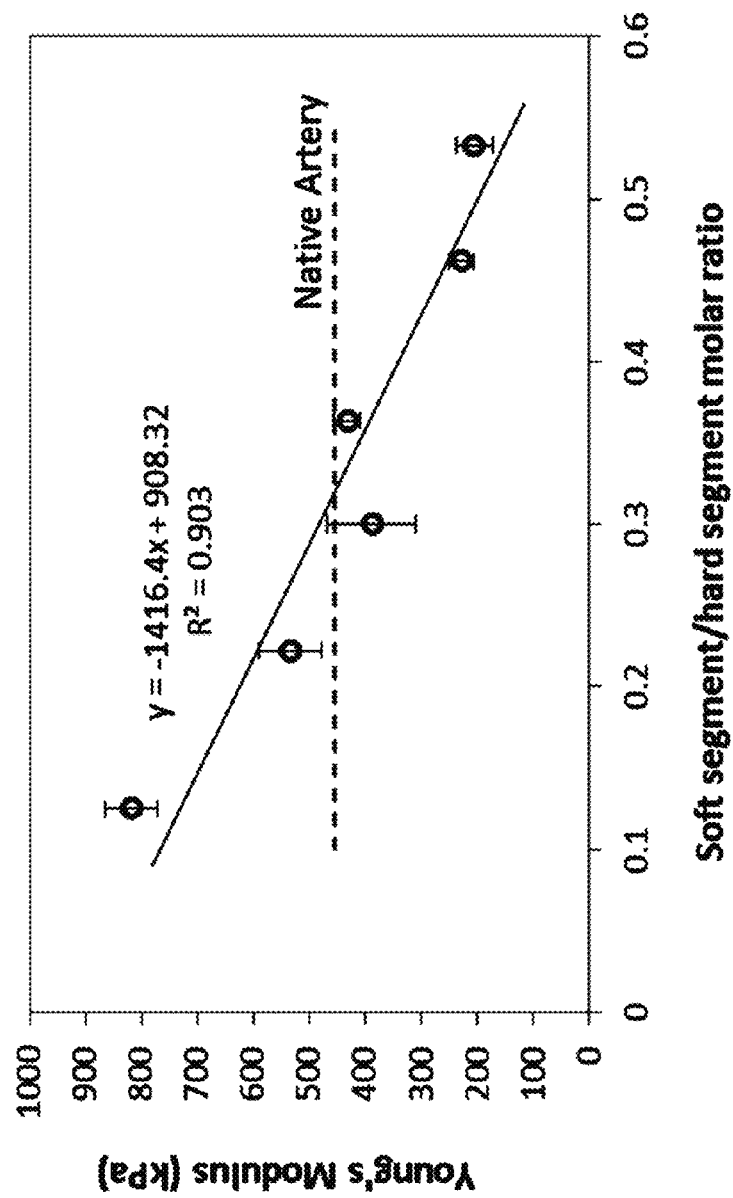
FIG. 4 demonstrates that the Young's Modulus of the porous material of the polymeric graft wall can be fine-tuned to match the Young's Modulus of various native blood vessels by varying the polymer composition, e.g., the ratio of the soft segments to hard segments in the polymer. The dotted line corresponds to the Young's Modulus of the native artery.
Figure 5A:
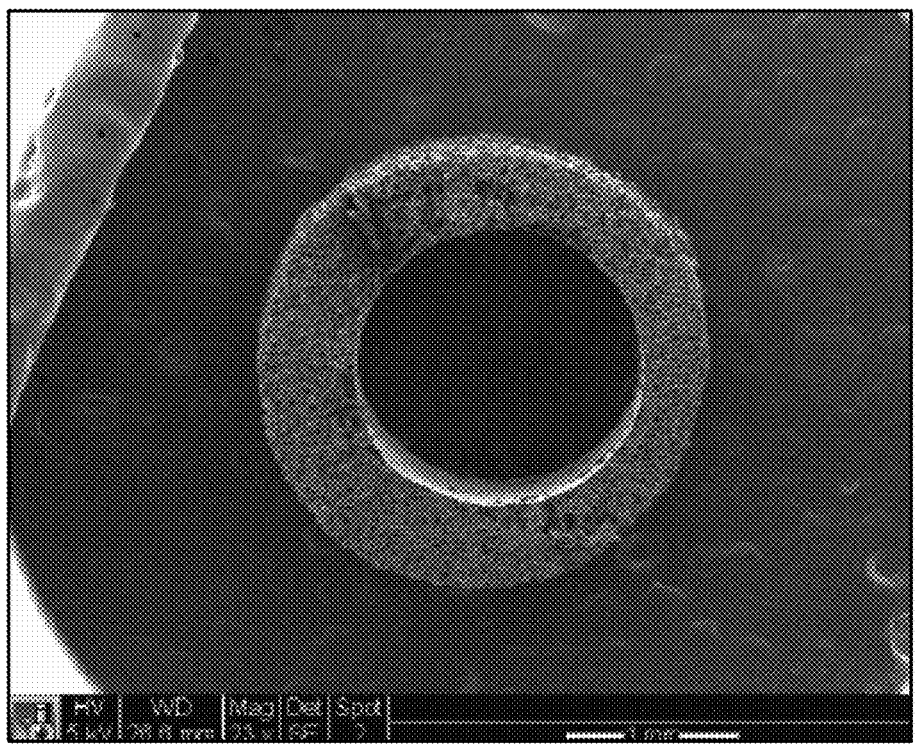
FIG. 5A is a SEM image of a cross-section of an exemplary graft (2 mm inner diameter) with a porous polyurethane graft wall that does not have a luminal coating layer.
Figure 5B:
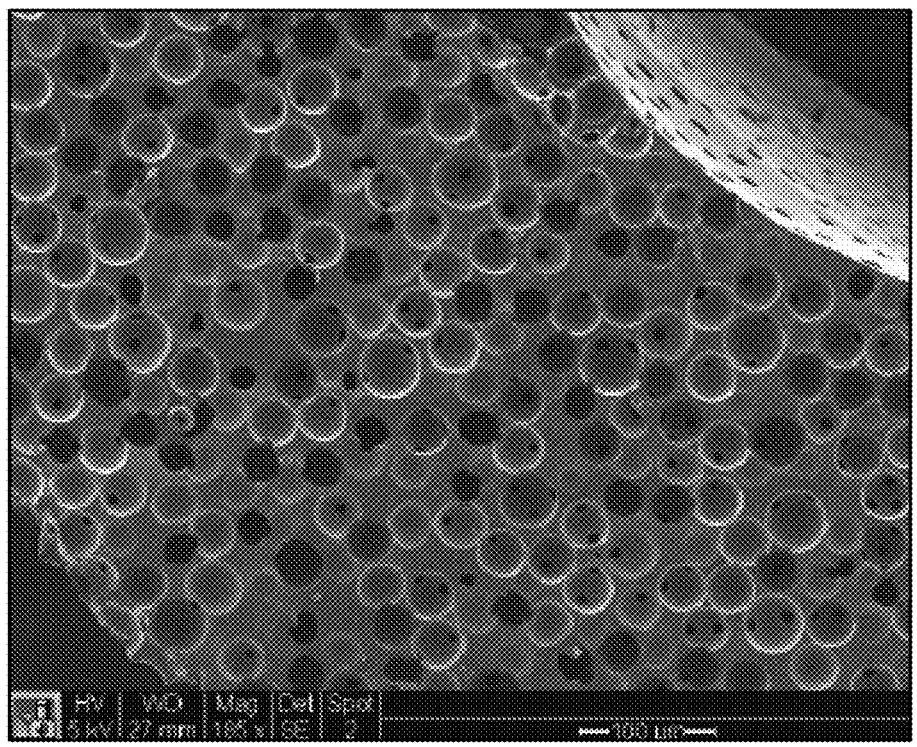
FIG. 5B is an enlarged SEM image of a part of the cross-section shown in FIG. 5A demonstrating the porous structure of the uncoated luminal surface of the graft (upper right corner).
Figure 5C:
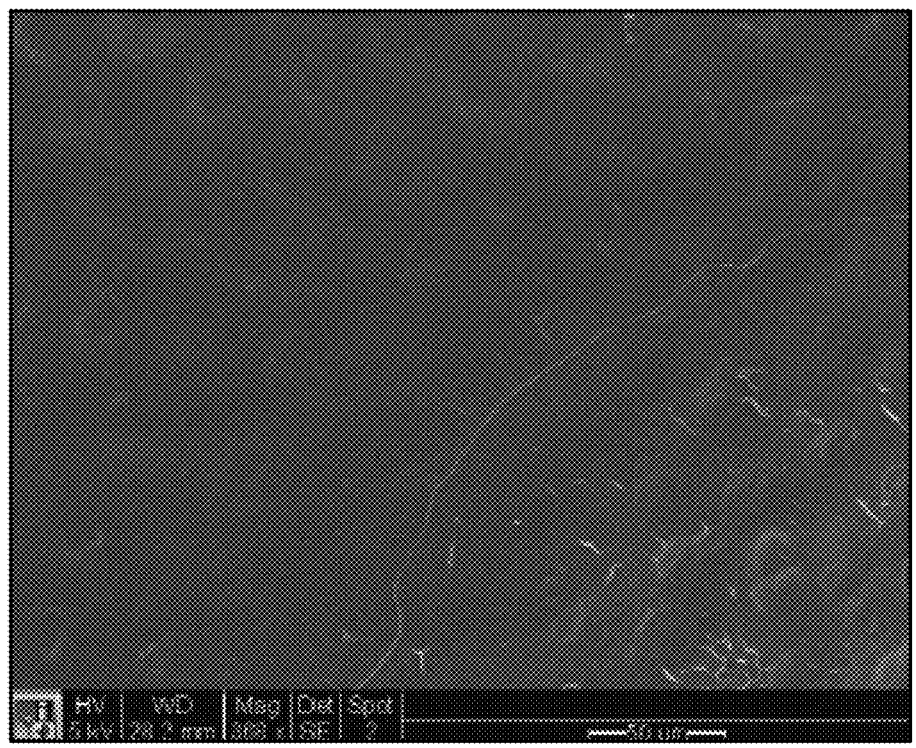
FIG. 5C is an SEM image of the luminal surface of a gelatin-coated pHEMA porous tube demonstrating that the coating blocks the pores and thus can prevent initial bleed out of the graft.
Figure 5D:
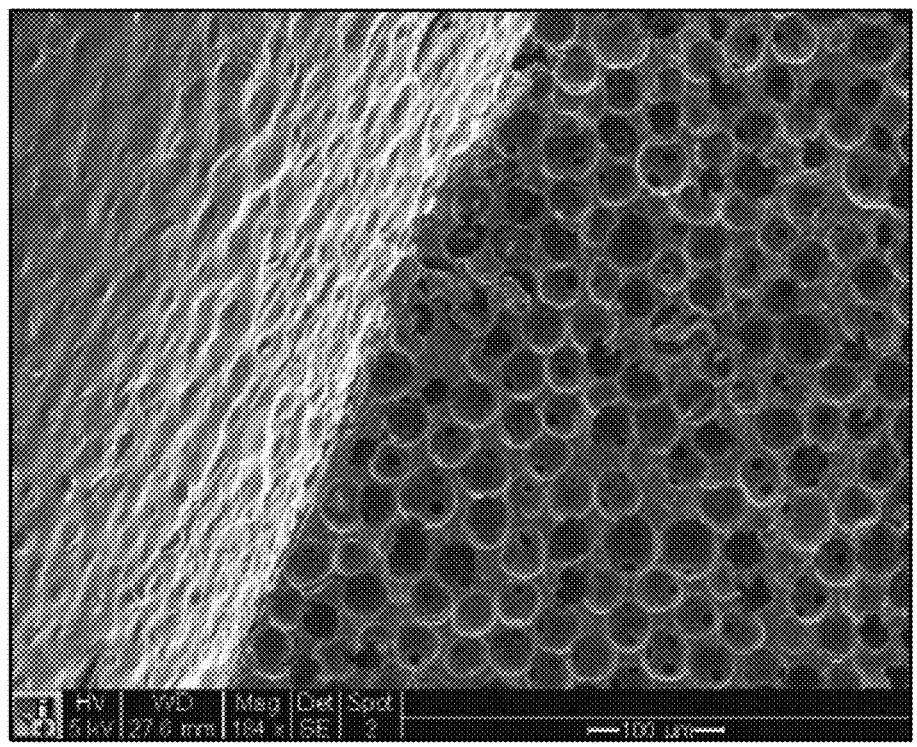
FIG. 5D is an SEM image of the wall and luminal surface of a gelatin-coated microporous pHEMA tube.
Figure 6A:
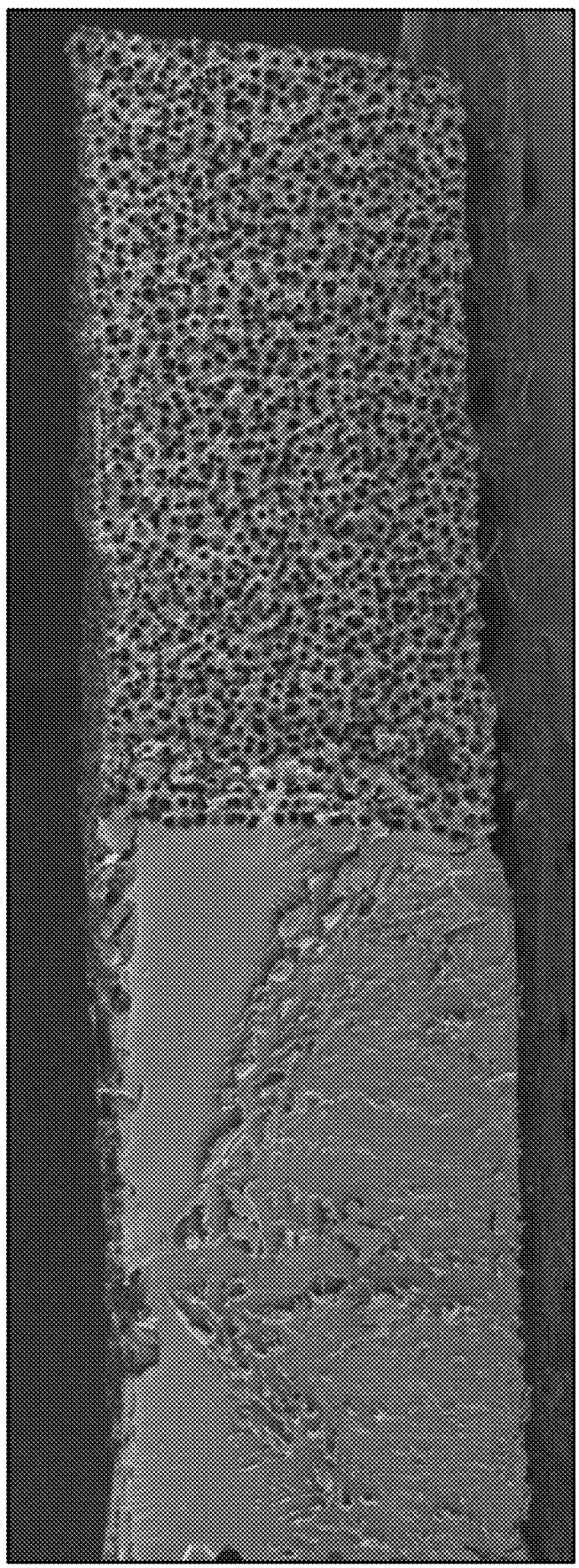
FIG. 6A is an SEM image of a polyurethane implant that has a non-porous section (left) and a microporous section that has interconnecting pores of average diameter 40 uM (right).
Figure 6B:
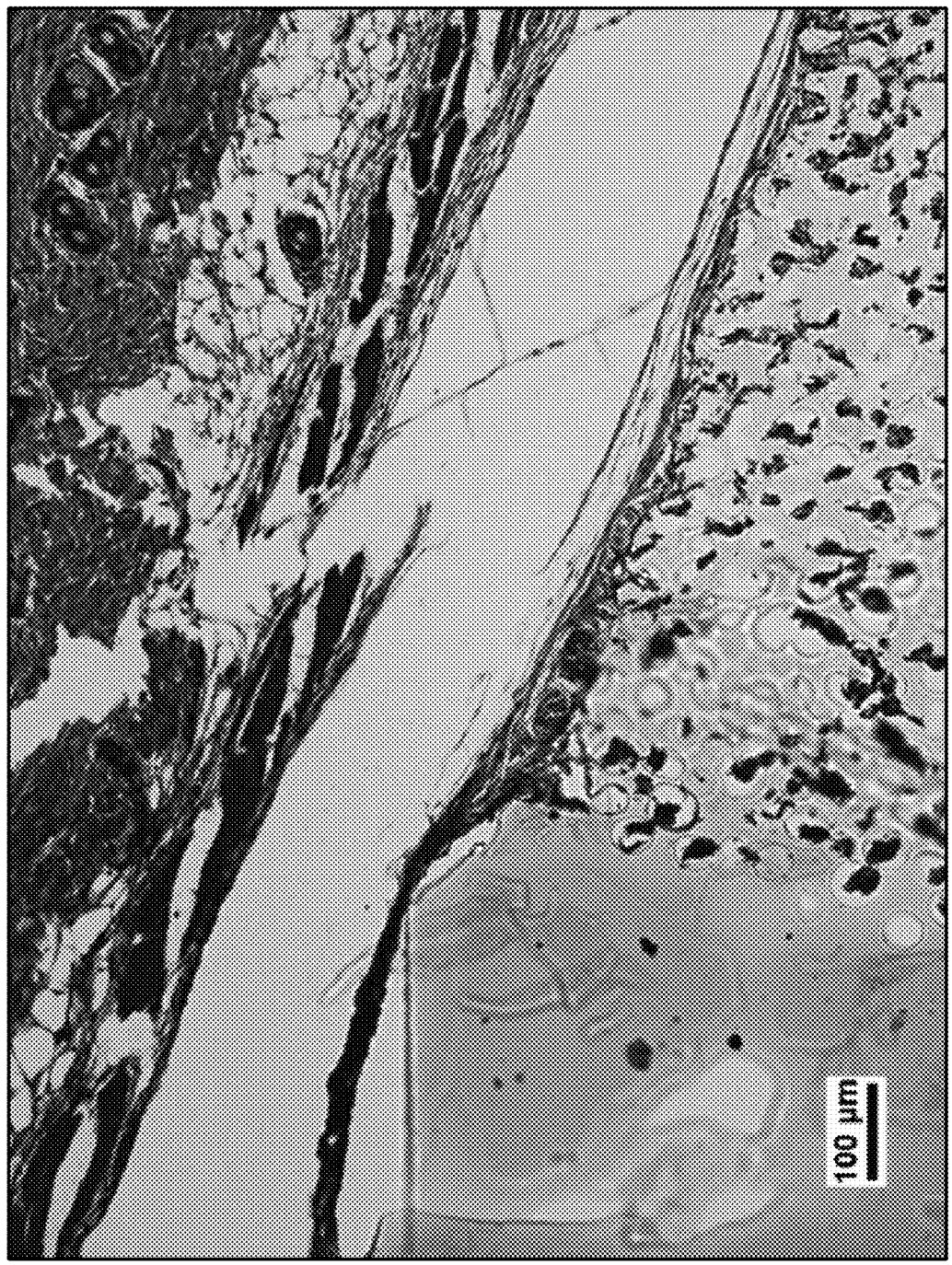
FIG. 6B is an SEM image of the material shown in FIG. 6A implanted into a mouse tissue demonstrating that the porous material mitigated local foreign body response while a collagen scar formed around the non-porous section (lower left).

In certain embodiments, elasticity of the of the polymeric material of the graft wall, e.g., its Young's Modulus, can be fine-tuned by varying the composition of the polymer, for example, by varying the molar ratio of soft segments to hard segments in the polyurethane. The Young's Modulus describes tensile elasticity, or the tendency of an object to deform along an axis when opposing forces are applied along that axis. As the material becomes more and more elastic, the Young's Modulus decreases. As shown in FIG. 4, materials with a range of Young's Modulus span from twice of that of the native artery to half of it can be obtained by varying the molar ratio of the soft segments to hard segments in the polyurethane polymer. Thus, a vascular graft that closely matches the elasticity of the blood vessel to be repaired, e.g., a native artery or a native vein, can be prepared by varying the molar ratio of the soft segments to hard segments in the polyurethane polymer of the graft wall. Additionally, if the vascular graft becomes more rigid after implantation, initial elasticity of the vascular graft can be fine-tuned, e.g., be more elastic than native blood vessels to compensate this change.

In some embodiments, the molar ratio of soft segments to hard segments is between about 0.1 to about 0.6, between about 0.1 and about 0.4, between about 0.125 and about 0.22, about 0.125, about 0.36, or about 0.22. At the ratio of 0.36, Young's Modulus matches that of the thoracic aorta (430 kPa); at the ratio of 0.125, the Young's Modulus matches that of the abdominal aorta (870 kPa); at the ratio between 0.125 and 0.22, the Young's Modulus covers the range from that of the femoral artery (690 kPa) to that of carotid artery (640) kPa. In certain embodiments, the polymeric graft wall has a Young's Modulus of between about 200 kPa and 850 kPa.

The vascular grafts of the invention comprise a layer of endothelial cell growth substrate on the luminal surface of the graft. In some embodiments, the endothelial cell growth substrate has thickness of between about 5 µm and about 500 µm. Examples of suitable endothelial cell growth substrates include gelatin, agarose gel, hydroxypropyl methylcellulose, albumin gel, and/or combinations thereof. In some embodiments, the endothelial cell growth substrate is biodegradable. In some embodiments, the endothelial cell growth substrate biodegrades when an endothelial cell lining is formed on the luminal surface of the implanted graft.

The endothelial cell growth substrate, e.g., gelatin, can be crosslinked. In some embodiments, the endothelial cell growth substrate can be covalently attached to the luminal surface of the graft wall, for example, the endothelial cell growth substrate can be crosslinked to the graft wall using one or more crosslinking chemistries known in the art. In other embodiments, the endothelial cell growth substrate is not covalently bound to the luminal surface of the graft wall.

In some embodiments, the graft wall of the vascular graft further comprises a reinforcement material embedded within the graft wall. In certain embodiments, the reinforcement material increases the burst strength of the graft, for example, over 1600 mm Hg. Methods for measurement of burst strength of a vessel are known in the art. In other embodiments, the polymeric graft wall does not comprise a reinforcement material, for example, when unreinforced polymer has the burst strength equal to or higher than that of a native blood vessel, e.g., over 1600 mm Hg.

In some embodiments, the reinforcement material is a non-degradable polymeric mesh, such as knitted mesh or woven mesh. Any suitable polymeric mesh material can be used as the reinforcement material, for example, polyester or ePTFE. In some embodiments, the graft wall has a suture strength comparable to or higher than that of a native blood vessel, for example, from about 0.5 N to about 5.0 N.

Figure 1A:
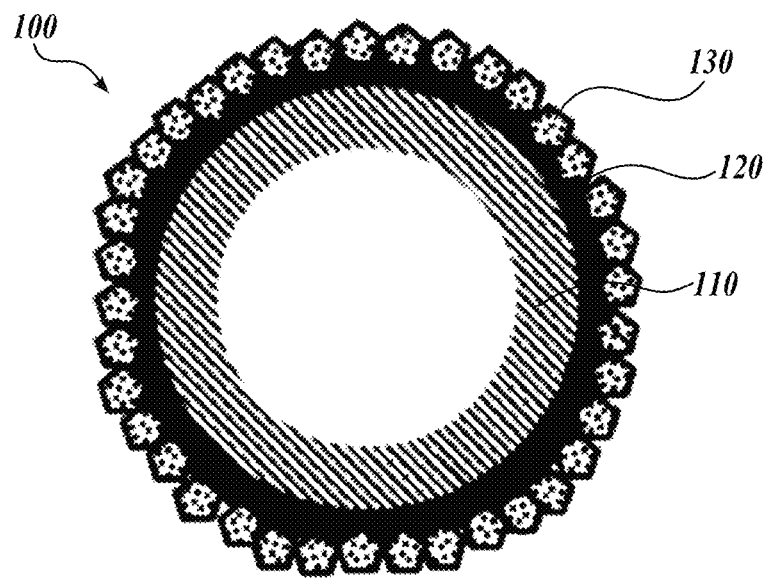
FIG. 1A is a schematic representation of a cross-section of a synthetic polymeric (ePTFE) vascular graft known in the art (100) showing the inner ePTFE graft wall (100) coated with an adhesive layer (120) which bonds a layer of microporous polymeric particles (130) to the ePTFE wall.

The grafts disclosed herein offer significant advantages compared to the known in the art grafts. FIG. 1A depicts an exemplary known in the art graft (100) comprising an ePTFE wall (110) which is impermeable to cells to prevent blood leakage from the blood vessel. A layer of adhesive (120) is applied to the outer surface of the wall which allows coating the graft with a layer of particles of microporous material (130), such as STAR material disclosed in WO 2015127254. Even though the microporous material promotes blood vessel growth through the material and minimizes foreign body response, the impermeable to blood vessel growth ePTFE wall (110) does not allow the blood vessels to reach the luminal surface of the graft.

Figure 1B:
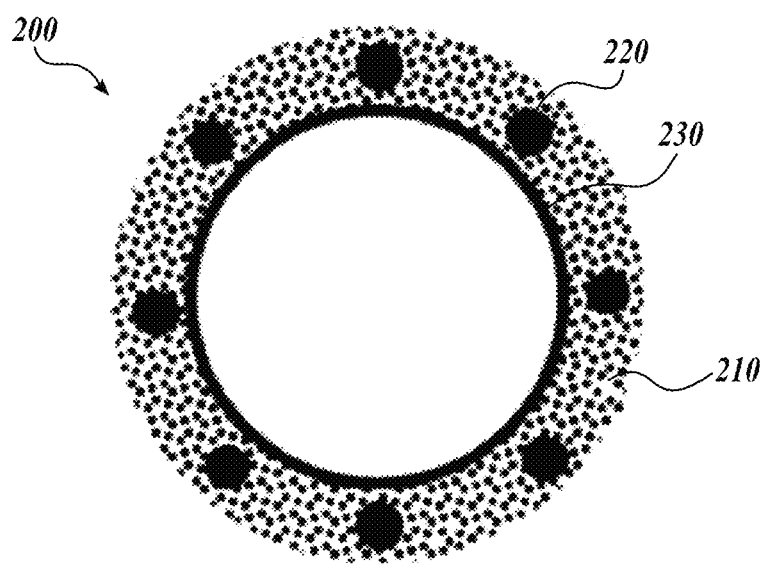
FIG. 1B is a schematic representation of a cross-section of an exemplary vascular graft (200) showing porous polymeric graft wall (210) with a layer of endothelial growth substrate coating the luminal surface (230) and polymeric mesh reinforcement (220) incorporated within the graft wall.

The inventors discovered that blood vessel growth through the graft wall is advantageous for endothelium healing and prevention of graft failure. FIG. 1B depicts an exemplary graft of the invention (200) having a microporous polymeric wall (210) reinforced by polymeric mesh (220) embedded within the wall (210) and having a coating of endothelial cell growth substrate (230) on the luminal surface of the graft. The interconnected microporous structure of the wall of the vascular graft promotes endothelial cell-rich blood vessel growth through the graft wall to the luminal surface. The thin endothelial cell growth substrate coating on the luminal surface of the graft offers the following advantages: first, it prevents initial bleeding out from the graft while still allowing endothelial cells from the outside to reach the luminal surface; second, it allows the desirable cytokines released by the pro-healing macrophages residing in the graft to diffuse through and attract endothelial cells from blood stream and adjacent vessels; third, it provides a matrix for inclusion of anti-thrombotic agents to address initial thrombogenicity of the graft. Additionally, the vascular graft of the invention wall is made of elastic and bio-stable polymer, for example, a crosslinked polyurethane, which allow dissipation of energy from pulsatile blood flow and promotes endothelium survival.

In some embodiments, the graft comprises the following elements: a network of interconnected pores spanning the graft wall from the outer surface to the luminal surface, wherein all pores are uniform in size and about 40 microns; a compliance (elasticity) similar to the native blood vessel; a biodegradable luminal surface that can assist in the regeneration of an endothelial cell lining. These elements are synergistic to achieve the healing needed for the long-term in vivo performance of the graft.

In some embodiments, the polymeric graft wall does not comprise an impermeable to blood vessels material layer. In other embodiments, the polymeric graft wall does not comprise a non-porous layer. In certain embodiments, the uncoated luminal surface of the polymeric graft wall is porous.

In addition to the above-described advantages, the vascular grafts disclosed herein have low thrombogenicity and are biocompatible. In certain embodiments, the graft is suturable, sterilizable, kink-resistant, and/or has a long shelf life.

In some embodiments, the endothelial cell growth substrate of the vascular grafts of the invention comprises an anti-thrombogenic agent. The anti-thrombogenic agent can be covalently or non-covalently immobilized within or on the surface of the endothelial growth substrate. In other embodiments, the anti-thrombogenic agent is embedded within the endothelial growth substrate and is released from the endothelial growth substrate. Any suitable anti-thrombogenic agent can be included. Examples of suitable anti-thrombogenic agents include heparin, disintegrin, hirudin, and combinations thereof. In some embodiments, the anti-thrombogenic agent is a small molecule, such as a small molecule inhibitor of thrombin.

In a second aspect, provided herein is a method of making a vascular graft disclosed herein comprising a porous polymeric graft wall and a luminal surface coated with a layer of endothelial cell growth substrate, the method comprising:

(a) coating a cylindrical rod having an outer surface and a first radius with a layer of an endothelial cell growth substrate to provide a coated rod;

(b) positioning the coated rod in the center of a tube having a second radius wherein the second radius is the inner radius of the tube and is greater than the first radius;

(c) filling the space between the outer surface of the coated rod and the inner wall of the tube with a polymer scaffold template comprising an array of monodisperse porogens, wherein substantially all the porogens have a similar diameter, wherein the mean diameter of the porogens is between about 25 micrometers and about 85 micrometers, wherein substantially all porogens are each connected to at least 4 other porogens, and wherein the diameter of substantially all the connections between the porogens is between about 15% and about 40% of the mean diameter of the porogens;

(d) forming a polymer around the template;

(e) removing the template to produce a porous polymeric graft wall, and (f) removing the rod and the tube, thereby forming the vascular graft.

In some embodiments of the method disclosed herein, the rod is a glass rod and the tube is a glass tube. In certain embodiments, the rod is coated with an endothelial substrate layer that has a thickness of between about 5 µm and about 500 µm.

The template used in the methods of the invention comprises an array of porogens. As used herein, the term "porogens" refers to any structures that can be used to create a template that is removable after the polymer is formed under conditions that do not destroy the polymer. Exemplary porogens that are suitable for use in the methods of the invention include, but are not limited to, polymer particles such as PMMA beads and polystyrene beads. The porogens can have any suitable shape that will permit the formation of a porous polymeric material with an array of pores, wherein substantially all the pores have a similar diameter, wherein the mean pore diameter is between about 25 and about 85 micrometers, wherein substantially all pores are each connected to at least 4 other pores, and wherein the diameter of substantially all the connections between the pores is between about 15% and about 40% of the mean diameter of the pores. For example, the porogens can be spherical.

The dimensions of the vascular grafts of the invention, for example, thickness of the graft wall, can be adjusted to match the thickness of the native blood vessel. In certain embodiments, the graft has a wall thickness substantially the same as a natural blood vessel. The first radius and the second radius can be selected in such a way that the difference between the first radius and the second radius is substantially the same as the thickness of a native blood vessel. Thus, by varying the first radius and the second radius, grafts having varying wall thickness can be prepared using the methods described herein.

Figure 7:
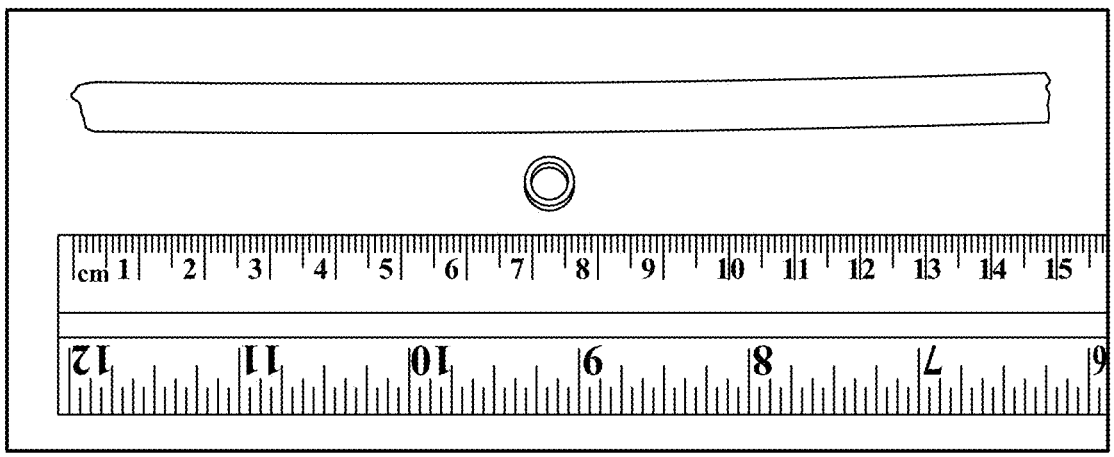
FIG. 7 is an illustration of an exemplary vascular graft (length 15 cm, inner diameter 6 mm) for implantation into a sheep model.
Figure 8:
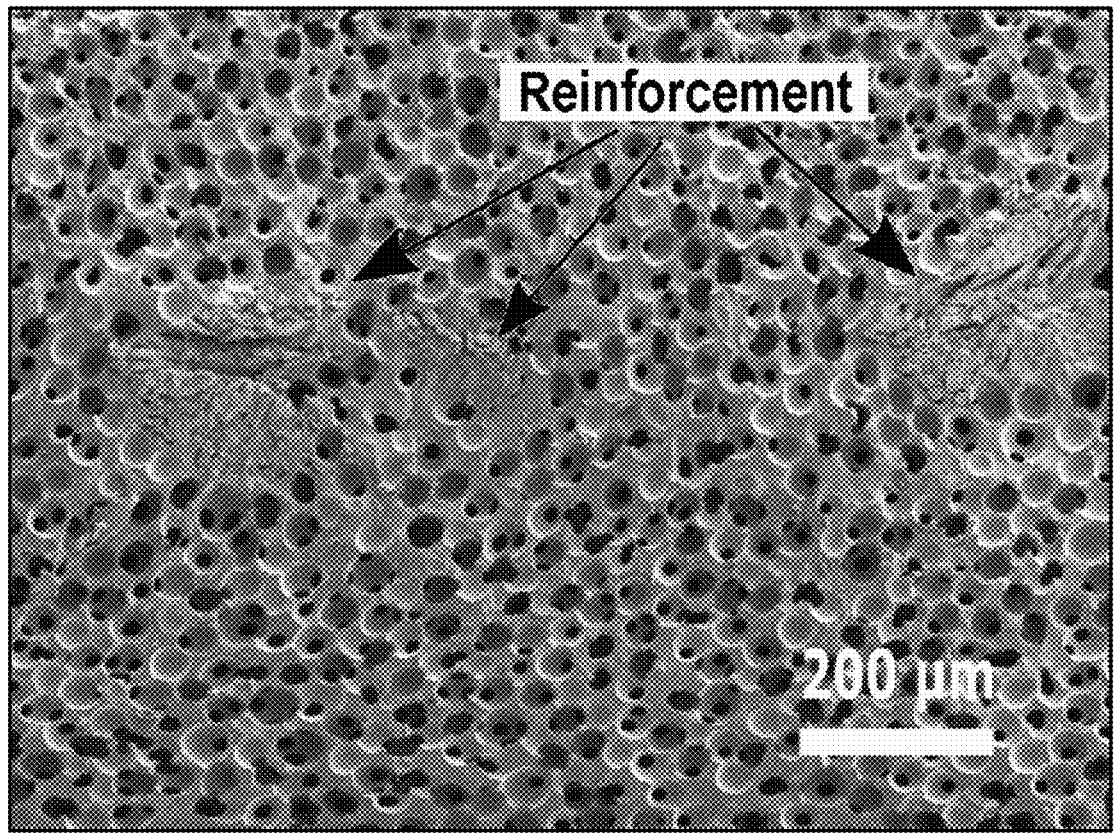
FIG. 8 is a SEM image of a cross-section of an exemplary polyurethane graft that has an embedded polyester reinforcement mesh.
Figure 9A:
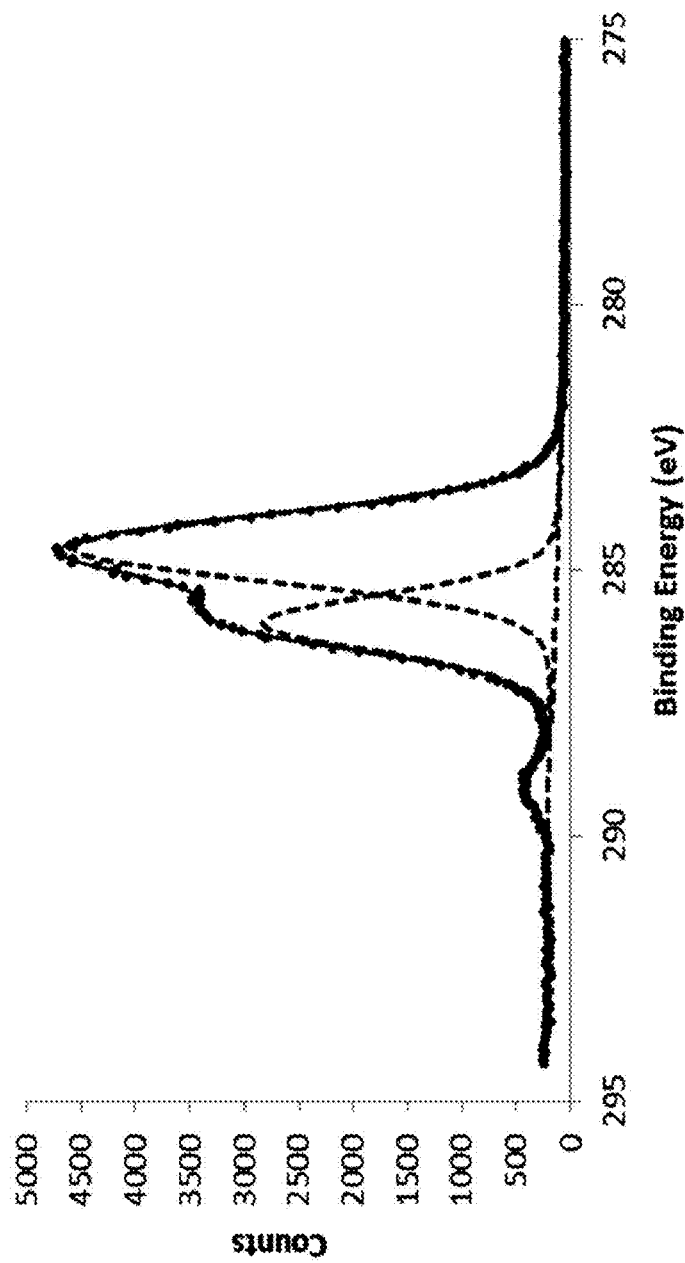
FIG. 9A is a high resolution ESCA spectrum showing peaks corresponding to carbon species of Pellethane 2363-80A material which has not been subjected to hydrogen peroxide treatment.
Figure 9B:
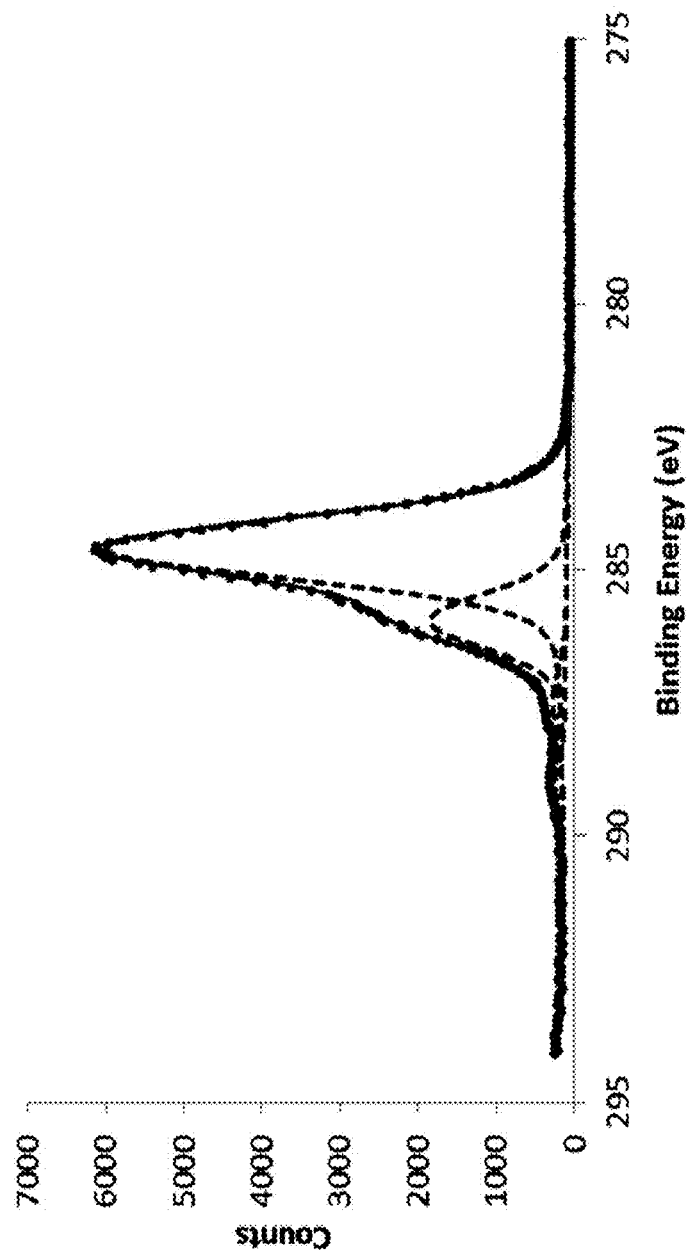
FIG. 9B is a high resolution ESCA spectrum showing peaks corresponding to carbon species of Pellethane 2363-80A material which was treated with hydrogen peroxide.
Figure 9C:
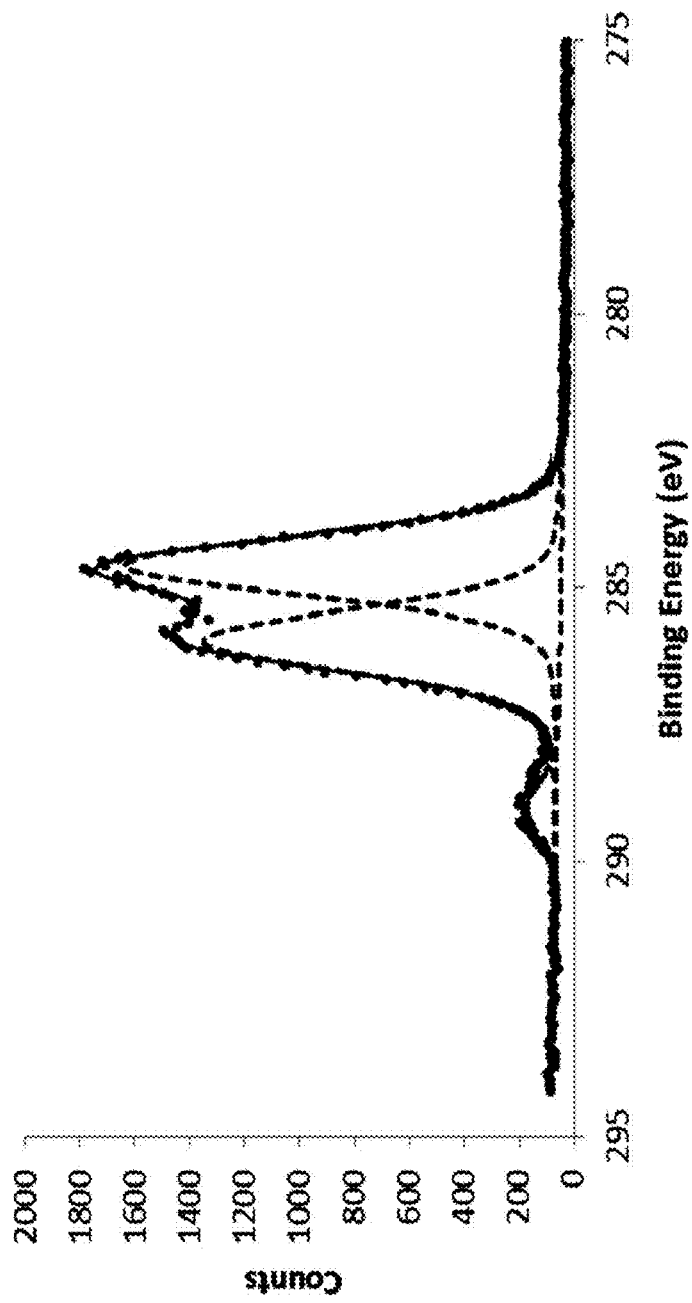
FIG. 9C is a high resolution ESCA spectrum showing peaks corresponding to carbon species of PU4344, an exemplary microporous vascular graft polyurethane material, which has not been subjected to hydrogen peroxide treatment.
Figure 9D:
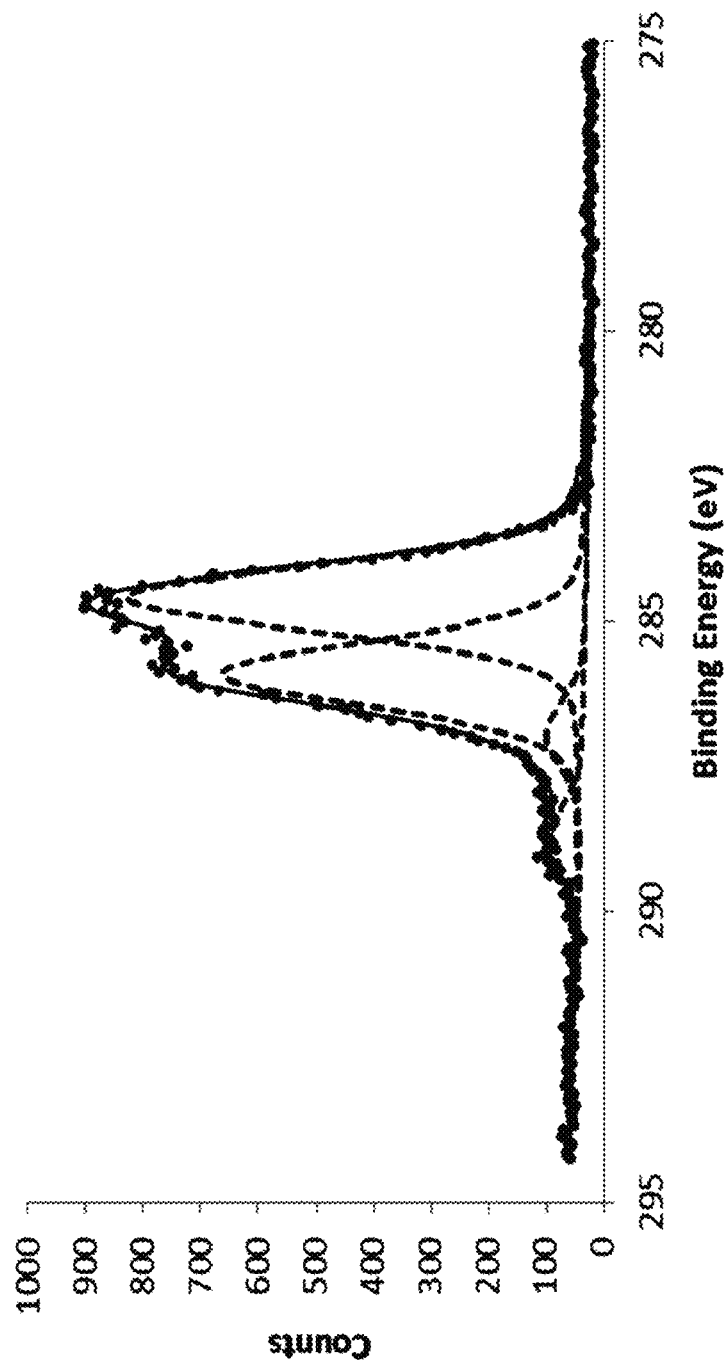
FIG. 9D is a high resolution ESCA spectrum showing peaks corresponding to carbon species of PU4344, an exemplary microporous vascular graft polyurethane material, after hydrogen peroxide treatment.

As used herein, a "native blood vessel" includes an artery and a vein. Examples of native blood vessels suitable for graft application include coronary arteries, including carotid, aortoiliac, infrainguinal, distal profunda femoris, distal popliteal, tibial, subclavian, and mesenteric arteries. In some embodiments, the vascular grafts disclosed herein have wall thickness of between about 0.12 mm to about 2 mm. In some embodiments, the grafts have an inner diameter between about 0.3 mm and about 4 cm. Any suitable length graft can be prepared using the methods described herein. For example, FIG. 7 depicts a graft designed to be implanted in a sheep model.

In a third aspect, provided herein is a method for treating vascular disease, comprising the step of implanting into a mammal in need of treatment a vascular graft, wherein the vascular graft comprises a polymeric graft wall having a luminal surface, wherein the graft wall has a plurality of interconnected pores, wherein each pore of the interconnected pores has a substantially uniform pore size, and wherein the mean diameter of the pores is between about 25 µm to about 85 µm, and the luminal surface is coated with a layer of endothelial cell growth substrate.

In some embodiments, the vascular graft comprises a crosslinked polyurethane graft wall having a luminal surface, wherein the graft wall has a plurality of interconnected pores, wherein each pore of the interconnected pores has a substantially uniform pore size, and wherein the mean diameter of the pores is between about 30 µm to about 50 µm, and the luminal surface is coated with a layer of endothelial cell growth substrate.

In some embodiments, the graft is implanted into a blood vessel, for example, during coronary artery bypass grafting (CABG), peripheral vascular bypass surgery, or carotid bypass surgery. In some embodiments, the mammal in need of treatment is a human. In certain embodiments, the vascular graft is implanted by directly connecting the vascular graft to a native blood vessel, for example, vascular graft is directly connected (e.g., by suturing) at the ends of the graft to the cut edges of a native vessel ("end-to-end") or to the side of the native vessel ("end-to-side").

Various embodiments of this invention are described herein, including the best mode known to the inventors for carrying out the invention. Variations, changes, modifications and substitution of equivalents on those embodiments will become apparent to those of ordinary skill in the art upon reading the foregoing description. The inventors expect skilled artisans to employ such variations, changes, modifications and substitution of equivalents as appropriate, and the inventors intend for the invention to be practiced otherwise than specifically described herein. Those of skill in the art will readily recognize a variety of non-critical parameters that could be changed, altered or modified to yield essentially similar results. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

EXAMPLES

Example 1: Synthetic Procedure for the Preparation of the Porous Polyurethane Material by Polymerization The polyurethane was synthesized using a mixture of poly (tetramethylene oxide) (PTMO, Mw=1000), 4,4'-methylene bis(phenyl isocyanate) (MDI), Desmodur N3200 (HTI), and 1,1,1-Tris(hydroxymethyl) propane (TMP) without a catalyst or a solvent. Poly(methyl methacrylate) (PMMA) beads with a broad size distribution were sieved to obtain monodispersity. For this experiment, all the PMMA beads were about 40 μm in diameter. The beads were loaded into the space between a 6-mm-diameter glass rod and 8-mm-inner-diameter glass tube which were held concentric by two custom-made Teflon stages at the ends. The bead-loaded tube was then sonicated for 1 hour to obtain close packing of the beads and then sintered at 175° C. for 20 hours to obtain interconnection between all adjacent beads. The bead cake was taken out of the glass tube and submerged in the freshly mixed polyurethane components. The resulting mixture was degassed under vacuum for 5 minutes. After purging with nitrogen, the bead cake and its internal space were filled with the polyurethane mixture. Then the bead cake was taken out of the mixture and wrapped with Teflon film, and the reaction mixture in the bead cake was allowed to polymerize at 55° C. for 48 hr. After the completion of the polymerization reaction, the PMMA template was solubilized by dichloromethane (DCM), leaving behind the precision-engineered porous vascular graft. After the vascular graft swelled in DCM and detached from the glass rod, DCM was gradually replaced with acetone, 70% ethanol, followed by deionized water to bring the graft to its original size.

Example 2: Procedure for Measurement of Young's Modulus

The vascular graft was cut open longitudinally with a pair of scissors and punched into a dumbbell shape. The Young's Modulus was determined using Instron 5543 instrument at extension rate of 10 mm/min in a water bath at 37° C. Suture strength was tested with one end of the vascular graft clamped to the bottom clamp of the Instron and sutured 2 mm from the other end with a single 5-0 Prolene suture which was tied to the top clamp. The suture was pulled at the rate of 2 mm/s at 37° C. in a water bath until its failure. Suture strength is the maximum force generated through the process.

With the inclusion of the reinforcement mesh, the suture strength of an exemplary material PU4344 (PTMO/MDI/HTI/TMP (molar ratio)=4/3/4/4) was 4.77±0.36 N, which is higher than the suture strength of native blood vessel (~2N). This indicates that the vascular graft has sufficient strength to be sutured to native blood vessels.

Example 3: Preparation of an Exemplary Graft

A reinforced graft was prepared by a procedure similar to the method described above in Example 1, except that the glass rod was wrapped with a polyester mesh before mounting on the Teflon stage, allowing the polyester mesh to be surrounded by the PMMA beads and ultimately embedded within the graft wall. To coat the luminal surface with gelatin, a 6-mm-diameter inner glass rod was dip-coated with gelatin. The luminal coating thickness can be controlled by the number of times of dip-coating. The glass rod was allowed to dry overnight then frozen at −80° C. for half an hour. The vascular graft was fitted onto the glass rod immediately after the coated rod was taken out of the freezer. The vascular graft-fitted glass rod was put into water briefly for the gelatin film to rehydrate and taken out, then heated to 60° C. in a vacuum oven allowing the gelatin coating to melt and to infiltrate into the pore openings on the luminal surface. The vascular graft-fitted glass rod was refrigerated overnight to allow the gelatin to re-gel. The gelatin film was crosslinked with EDC/NHS chemistry. The vascular graft was submerged into a mixture of xylene and 70% ethanol to allow it to swell and to detach from the glass rod. The gelatin film remained on the luminal surface of the vascular graft. The solvent was gradually switched to 70% ethanol followed by deionized water to recover the graft size.

Example 4: Implantation of Porous Polyurethane Material into Mouse Tissue and Staining of the Tissue to Demonstrate that the Polyurethane Material Mitigates FBR Polyurethane discs (8-mm wide) with a 2-mm wide nonporous stripe in the middle separating the two sectors of 40 μm and 100 μm porous structures were implanted in 8-10-week old 028 BALB/cAnNCrl mice (Charles River Laboratories) subcutaneously for 3 weeks. The disks were harvested with the surrounding tissue, fixed in zinc fixative, embedded in paraffin, and sliced into 6 μm sections. Masson's trichrome stain was used to assess FBC. Vascularization was evaluated by immune-enzyme staining with a panendothelial antigen, MECA 32 (BD Pharmingen™, 550563, 1:30).

Example 5: Biostability Testing of the Grafts

In vivo, macrophages constantly try to attack and break down foreign materials by releasing peroxide species. Hydrogen peroxide treatment has been shown to accurately mimic long-term degradation behavior of polyurethane in vivo. For in vitro biostability test, a small piece of exemplary non-porous polyurethane (PTMO/MDI/HTI/TMP (molar ratio)=4/3/4/4, referred to as PU4344) was submerged in 30% hydrogen peroxide at 37° C. for 24 hours then dried under vacuum. As a control, a piece of the same material was submerged in deionized water at 37° C. for 24 hours then dried under vacuum. Commercially available "biostable" polyurethane Pellethane 2363-80A was dissolved in DMF then precipitated in methanol. This process was repeated to remove all processing aides and stabilizers in the material. The Pellethane was then dissolved in DMAc at a concentration of 50 mg/ml. A 50 μL aliquot of the solution was pipetted onto 10-mm microcoverslip and allowed to dry at 55° C. This process was repeated until the Pellethane film on the coverslip reached 12 mg. Two samples of Pellethane film were treated in deionized water or in 30% hydrogen peroxide as described above for PU4344. X-ray Photoelectron Spectroscopy (XPS) spectra of the samples were taken on a Surface Science Instruments S-Probe photoelectron spectrometer with a monochromatized Al Kα X-ray source which was operated at 20 mA and 10 kV. X-ray analysis area for these acquisitions was approximately 800 mm across. Pressure in the analytical chamber during spectral acquisition was less than 5×10⁻⁹ torr. Pass energy for high resolution spectra was 50 eV. Data point spacing was 0.065 eV/step for high resolution spectra. The take-off angle (the angle between the sample normal and the input axis of the energy analyzer) was 0°, (0° take-off angle≈100 Å sampling depth). Service Physics Hawk version 7 data analysis software was used for data analysis. The results are summarized in Table 1 and in FIGS. 9A-D.

X-ray Photoelectron Spectroscopy (XPS), also known as Electron Spectroscopy for Chemical Analysis (ESCA), probes the outer 10 nm surface of material and thus is extremely sensitive to surface change. For these reasons, peroxide treatment followed by examination by ESCA was chosen to test the biostability in vitro. It can be seen that after hydrogen peroxide treatment, the C—O composition of Pellethane significantly decreases while that of the PU4344 only decreases modestly. Both materials show an emerging C=O peak indicating oxidation. The decrease of C—O composition in PU4344 is almost the sample as the increase of C=O, indicating a conversion from C—O to C=O through oxidation. However, both carbon and oxygen stay on the surface. On the contrary, in the hydrogen peroxide-treated Pellethane sample, the loss of C—O is replaced by C—C composition. This may indicate that the oxidation was so severe that chains of the C—O rich soft segment were cleaved and left the surface, leaving behind more C—C rich hard segments. Overall, this result demonstrates that PU4344 has better biostability than Pellethane 2363-80A.

TABLE 1

Composition of different carbon species of control and treated polyurethanes.

| Carbon species | Pellethane 2363-80A | | PU4344 | |
|---|---|---|---|---|
|  | Control | $H_2O_2$ treated | Control | $H_2O_2$ treated |
| C—C (hydrocarbon) | 64.227 | 76.521 | 52.459 | 51.769 |
| C—O (ether) | 33.713 | 20.593 | 44.286 | 40.884 |
| C=O (carbonyl) | 0 | 0.886 | 0 | 4.11 |
| N—C=O (urethane) | 2.057 | 1.991 | 3.255 | 3.238 |

Example 6: Implantation of Graft into Sheep

The vascular graft was prepared as described above. FIG. 7 shows an exemplary graft designed for implantation in a sheep model. The graft is sterilized with 70% ethanol then stored in sterile PBS for two weeks. Endotoxin and cytotoxicity are tested prior to the implantation. The graft is implanted into a blood vessel of a sheep following literature procedure (Ted R. Kohler and Thomas R. Kirkman. Dialysis access failure: a sheep model of rapid stenosis. *Journal of Vascular Surgery*, 30:744-51 (1999)).

While illustrative embodiments have been illustrated and described, it will be appreciated that various changes can be made therein without departing from the spirit and scope of the invention.

The invention claimed is:

1. A vascular graft comprising a polymeric graft wall having a luminal surface adapted for contact with blood flow,
   wherein a Young's Modulus of the polymeric graft wall is configured to match a Young's Modulus of a native blood vessel,
   wherein the polymeric graft wall has a burst pressure over 1600 mm Hg,
   wherein the polymeric graft wall comprises a crosslinked polyurethane comprising one or more soft segments and one or more hard segments;
   wherein the graft wall has interconnected pores from the outer surface to the luminal surface of the graft wall, each pore of the interconnected pores has a substantially uniform pore size, each pore of the interconnected pores is spherical, and the pore size is in the range from about 25 μm to about 85 μm;
   wherein the luminal surface is coated with a layer of endothelial cell growth substrate;
   wherein the polymeric graft wall comprises a reinforcement material incorporated within the polymeric graft wall and extending longitudinally along the graft wall; and
   wherein the interconnected microporous structure of the wall of the vascular graft promotes endothelial cell-rich blood vessel growth and healing through the graft wall to the luminal surface.

2. The vascular graft of claim 1, wherein one or more soft segments comprises poly(tetramethylene oxide) (PTMO), poly(ethylene oxide), poly(propylene oxide), hydroxyl terminated polydimethylsiloxane (PDMS), hydroxyl terminated poly(isoprene), hydroxyl terminated polyisobutylene, hydroxyl terminated fluoropolymer, hydroxyl terminated polysilane, or combinations thereof.

3. The vascular graft of claim 1, wherein one or more hard segments comprises a residue of a compound selected from the group consisting of 2,2'-methylene diphenyl diisocyanate, 2,4'-methylene diphenyl diisocyanate, 4,4'-methylene diphenyl diisocyanate, (MDI), toluene diisocyanate (TDI), 1,4-phenylene diisocyanate, 1,3-phenylene diisocyanate, m-xylene diisocyanate, trans-1,4-cyclohexylene diisocyanate, naphthalene 1,5-diisocyanate (NDI), 1,4-diisocyanatobutane, 1,6-hexamethylene diisocyanate (HDI), 1,8-diisocyanatooctane, isophorone diisocyanate (IPDI), 4,4'-dicyclohexylmethane diisocyanate (H12MDI), 4,5-dibromobenzene-1,2-diol, 5-nitro-m-xylene-α,α'-diol, 2-nitro-2-phenyl-propane-1,3-diol, trans-2,3-dibromo-2-butene-1,4-diol, and combinations thereof.

4. The vascular graft of claim 1, wherein the crosslinked polyurethane comprises one or more residues of a crosslinker selected from 6-[3-(6-isocyanatohexyl)-2,4-dioxo-1,3-diazetidin-1-yl] hexyl N-(6-isocyanatohexyl) carbamate (HTI), 1,1,1-tris(hydroxymethyl) propane (TMP), tris(hydroxymethyl) nitromethane, tris(4-isocyanatophenyl) thiophosphate (TI), undecane-1,6,11-triyl triisocyanate (UTI), triphenylmethane-4,4',4''-triisocyanate (TPTI), glycerol, 1,2,6-hexanetriol, hexane-1,3,5-triol, pentaerythritol (PT), and a combination thereof.

5. The vascular graft of claim 3, wherein the polyurethane is prepared by co-polymerization of poly(tetramethylene oxide), 4,4'-methylene diphenyl diisocyanate, 6-[3-(6-isocyanatohexyl)-2,4-dioxo-1,3-diazetidin-1-yl] hexyl-N-(6-isocyanatohexyl) carbamate, and 1,1,1-tris(hydroxymethyl) propane.

6. The vascular graft of claim 1, wherein the molar ratio of soft segments to hard segments is between about 0.1 to about 0.6, between about 0.1 and about 0.4, between about 0.125 and about 0.22, about 0.125, about 0.36, or about 0.22.

7. The vascular graft of claim 1, wherein pore size is in the range from about 30 μm to about 50 μm.

8. The vascular graft of claim 1, wherein the layer of endothelial cell growth substrate has thickness of between about 5 μm and about 500 μm.

9. The vascular graft of claim 1, wherein the endothelial cell growth substrate comprises gelatin, agarose gel, hydroxypropyl methylcellulose, or albumin gel.

10. The vascular graft of claim 1, wherein the endothelial growth substrate comprises an anti-thrombogenic agent.

11. The vascular graft of claim 1, wherein the reinforcement material is a non-degradable polymeric mesh.

12. The vascular graft of claim 11, wherein the non-degradable polymeric mesh is knitted mesh or woven mesh.

13. The vascular graft of claim 1, wherein the reinforcement material comprises polyester or ePTFE.

14. The vascular graft of claim 1, wherein the graft wall has suture strength from about 0.5 N to about 5.0 N.

15. The vascular graft of claim 1, wherein the polyurethane has a Young's Modulus between about 200 kPa and 850 kPa.

16. A method for treating vascular disease, comprising implanting into a mammal in need of treatment a vascular graft of claim 1.

17. A vascular graft comprising a polymeric graft wall having a luminal surface adapted for contact with blood flow, wherein the graft wall has interconnected pores from the outer surface to the luminal surface of the graft wall, and wherein the pores of the interconnected pores are spherical, have a substantially uniform pore size, have a pore size in the range from about 25 μm to about 85 μm, and have a difference in diameter between two pores of less than about 20% of the diameter of a larger pore of the two pores;

wherein a Young's Modulus of the polymeric graft wall is configured to match a Young's Modulus of a native blood vessel, wherein the polymeric graft wall has a burst pressure over 1600 mm Hg, and wherein the polymeric graft wall comprises a crosslinked polyurethane comprising one or more soft segments and one or more hard segments; and wherein the interconnected microporous structure of the wall of the vascular graft promotes endothelial cell-rich blood vessel growth and healing through the graft wall to the luminal surface.

* * * * *

UNITED STATES PATENT AND TRADEMARK OFFICE
CERTIFICATE OF CORRECTION

PATENT NO. : 12,194,196 B2  
APPLICATION NO. : 16/861104  
DATED : January 14, 2025  
INVENTOR(S) : Buddy D. Ratner et al.

Page 1 of 1

It is certified that error appears in the above-identified patent and that said Letters Patent is hereby corrected as shown below:

In the Claims

| Column | Line | |
|---|---|---|
| 14 | 53 | Claim 5, delete "claim 3," and insert -- claim 1, -- |

Signed and Sealed this  
Third Day of February, 2026

John A. Squires  
*Director of the United States Patent and Trademark Office*